(12) United States Patent
Chen

(10) Patent No.: US 10,750,790 B2
(45) Date of Patent: *Aug. 25, 2020

(54) ELECTRONIC CIGARETTE AND ATOMIZING ASSEMBLY AND ATOMIZING ELEMENT THEREOF

(71) Applicant: Shenzhen Smoore Technology Limited, Shenzhen, Guangdong (CN)

(72) Inventor: Zhiping Chen, Guangdong (CN)

(73) Assignee: Shenzhen Smoore Technology Limited, Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/662,149

(22) Filed: Oct. 24, 2019

(65) Prior Publication Data

US 2020/0054077 A1 Feb. 20, 2020

Related U.S. Application Data

(63) Continuation of application No. 15/860,822, filed on Jan. 3, 2018, now Pat. No. 10,492,539, which is a continuation of application No. 14/985,658, filed on Dec. 31, 2015, now Pat. No. 9,888,722.

(30) Foreign Application Priority Data

Oct. 22, 2015 (CN) .......................... 2015 1 0690956
Nov. 27, 2015 (CN) .......................... 2015 1 0854348

(51) Int. Cl.
*A24F 47/00* (2020.01)
*H05B 3/44* (2006.01)
*F16J 15/02* (2006.01)
*H05B 3/12* (2006.01)
(Continued)

(52) U.S. Cl.
CPC .............. *A24F 47/008* (2013.01); *A24F 7/00* (2013.01); *F16J 15/021* (2013.01); *H05B 3/12* (2013.01); *H05B 3/44* (2013.01); *A24F 40/46* (2020.01); *H05B 2203/013* (2013.01); *H05B 2203/017* (2013.01); *H05B 2203/021* (2013.01); *H05B 2203/022* (2013.01)

(58) Field of Classification Search
CPC .................................................. A24F 47/008
See application file for complete search history.

(56) References Cited

U.S. PATENT DOCUMENTS

2011/0226236 A1* 9/2011 Buchberger ............ A24F 40/44
128/200.23
2012/0279512 A1* 11/2012 Hon ....................... A61M 15/06
131/329

(Continued)

FOREIGN PATENT DOCUMENTS

CN 201938355 U 8/2011
CN 203435687 U 2/2014
(Continued)

*Primary Examiner* — Eric Yaary
(74) *Attorney, Agent, or Firm* — Coats & Bennett, PLLC

(57) ABSTRACT

An atomizing element for an electronic cigarette is provide, which includes: a porous body comprising an atomizing surface and a liquid absorbing surface; and a porous heating film formed on the atomizing surface. An electronic cigarette and an atomizing assembly including the same are also provided.

20 Claims, 9 Drawing Sheets

(51) Int. Cl.
*A24F 7/00* (2006.01)
*A24F 40/46* (2020.01)

(56) References Cited

U.S. PATENT DOCUMENTS

| | | | | |
|---|---|---|---|---|
| 2013/0255702 A1* | 10/2013 | Griffith, Jr. | ............ | A24F 47/008 131/328 |
| 2014/0060554 A1* | 3/2014 | Collett | ................... | H05B 3/265 131/328 |
| 2014/0069424 A1* | 3/2014 | Poston | .................. | A24F 47/008 128/202.21 |
| 2014/0182611 A1* | 7/2014 | Liu | ....................... | A24F 47/008 131/329 |
| 2016/0135505 A1 | 5/2016 | Li et al. | | |
| 2017/0027225 A1* | 2/2017 | Buchberger | ......... | A61M 11/042 |
| 2017/0035109 A1* | 2/2017 | Liu | .......................... | H05B 3/24 |

FOREIGN PATENT DOCUMENTS

| | | |
|---|---|---|
| CN | 203467677 U | 3/2014 |
| CN | 203776165 U | 8/2014 |
| CN | 104522891 A | 4/2015 |

\* cited by examiner

ELECTRONIC CIGARETTE AND ATOMIZING ASSEMBLY AND ATOMIZING ELEMENT THEREOF

This application is a continuation application of U.S. patent application Ser. No. 15/860,822, filed Jan. 3, 2018, entitled, "ELECTRONIC CIGARETTE AND ATOMIZING ASSEMBLY AND ATOMIZING ELEMENT THEREOF", which is a continuation application of U.S. Pat. No. 9,888,722, filed Dec. 31, 2015 entitled, "ELECTRONIC CIGARETTE AND ATOMIZING ASSEMBLY AND ATOMIZING ELEMENT THEREOF", which claims the benefit of Chinese Patent Application No. 2015106909563, filed Oct. 22, 2015, and Chinese Patent Application No. 2015108543481, filed Nov. 27, 2015, the contents of which are incorporated by reference herein in their entirety for all purposes.

FIELD OF THE INVENTION

The present disclosure relates to an electronic cigarette and an atomizing assembly and an atomizing element thereof.

BACKGROUND OF THE INVENTION

Electronic cigarettes, also known as virtual cigarette or electronic atomizers, are a cigarette substitute for smoking cessation. The electronic cigarette has a similar appearance and taste as the cigarette, but it generally does not contain harmful ingredients of the cigarettes, such as tar, suspended particles, and so on.

The electronic cigarette is mainly composed of an atomizer and a power assembly. The atomizer is the core device of the electronic cigarette to generate atomizing gas; the quality and taste of the smoke are dependent on the atomization effect. A conventional heating element of the atomizer is a spiral resistance wire wrapped around a wicking material. When activated, the resistance wire quickly heats up thus turning the liquid absorbed by the wicking material into a vapor, which is then inhaled by the user.

However, during use of this conventional electronic cigarette, only the liquid located close to a heating wire can be heated and atomized, while the atomization effect of the liquid located away from the heating wire or in the gap between the spiral heating wire is poor. Additionally, as the distance of the heating wire increases, the temperature will drop greatly, which results in uneven atomizing particles and deteriorates the atomizing effect.

SUMMARY OF THE INVENTION

The present disclosure is directed to an electronic cigarette and an atomizing assembly and an atomizing element thereof having a better atomizing performance.

An atomizing element for an electronic cigarette includes: a porous body comprising an atomizing surface and a liquid absorbing surface; and a porous heating film formed on the atomizing surface.

An atomizing assembly for an electronic cigarette includes: a housing defining an airflow channel therein and comprising a reservoir for storing liquid; an atomizing core connected to the housing, wherein the atomizing core includes the foregoing atomizing element; wherein the airflow channel is in fluid communication with the atomizing surface, and the reservoir is in fluid communication with the liquid absorbing surface.

An electronic cigarette includes a power supply assembly and the foregoing atomizing assembly, wherein the power supply assembly is electrically coupled to the atomizing element of the atomizing assembly.

The porous body of the aforementioned atomizing element can block the liquid while ensure the liquid guiding effect. The plurality of micropores on the porous heating film can increase a contact area for the liquid, thus enhancing an atomizing effect. Since the porous heating film is located on the atomizing surface of the porous body, the atomized liquid can be exhausted from the porous body. The porous heating film can further enable the porous body to be heated uniformly, therefore the temperature of the porous body evenly increases at all part, and the problem of generating large atomized particles due to low temperature at local portion can be avoided, thus the taste of the electronic cigarette can be improved due to the uniform atomized particles.

These and other objects, advantages, purposes and features will become more apparent upon review of the following specification in conjunction with the drawings.

BRIEF DESCRIPTION OF THE DRAWINGS

The components in the drawings are not necessarily drawn to scale, the emphasis instead being placed upon clearly illustrating the principles of the present disclosure. Moreover, in the drawings, like reference numerals designate corresponding parts throughout the views.

DETAILED DESCRIPTION OF THE EMBODIMENTS

Reference will now be made to the drawings to describe, in detail, embodiments of the present electronic cigarette and an atomizing assembly and an atomizing element thereof. It should be noted that references to "an" or "one" embodiment in this disclosure are not necessarily to the same embodiment, and such references mean at least one.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list.

Figure 1:
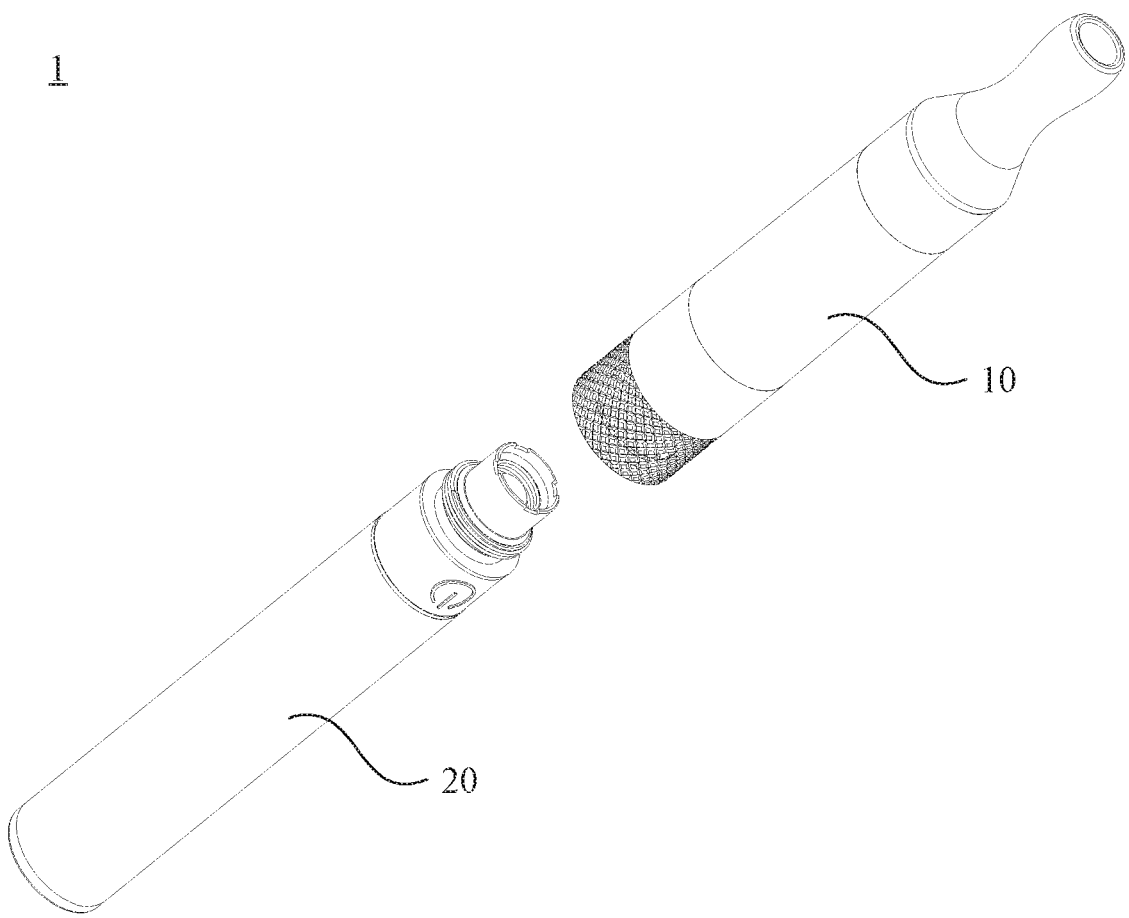
FIG. 1 is an exploded, perspective view of an electronic cigarette in accordance with one embodiment.
Figure 2:
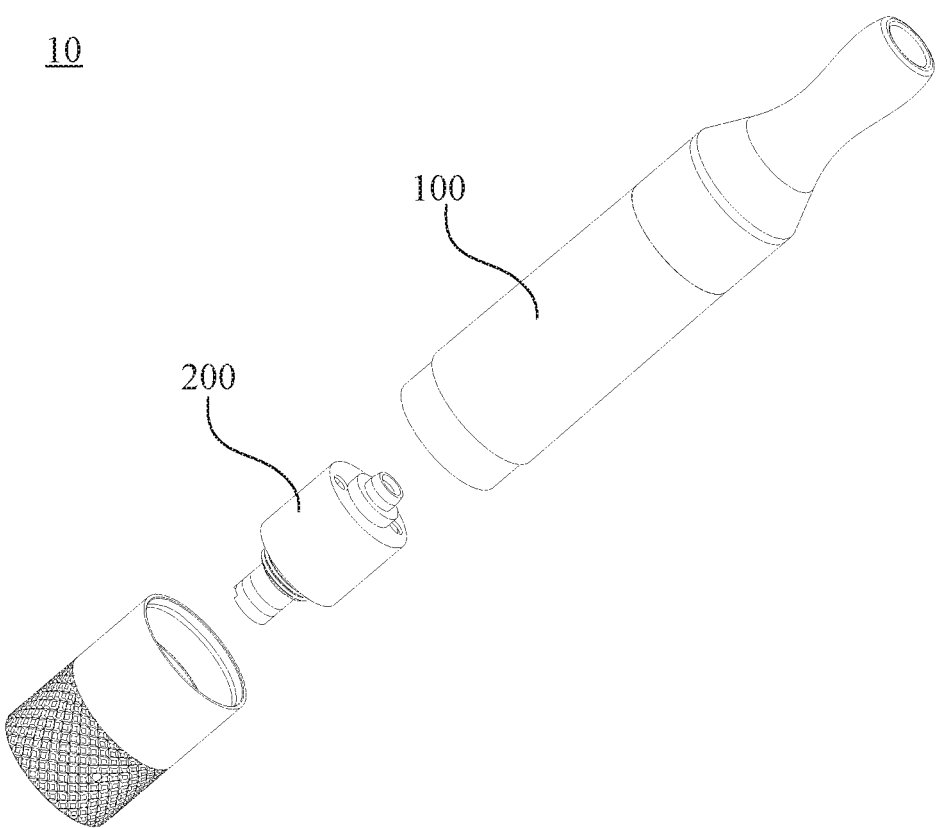
FIG. 2 is a partial exploded, perspective view of the electronic cigarette of FIG. 1.
Figure 3:
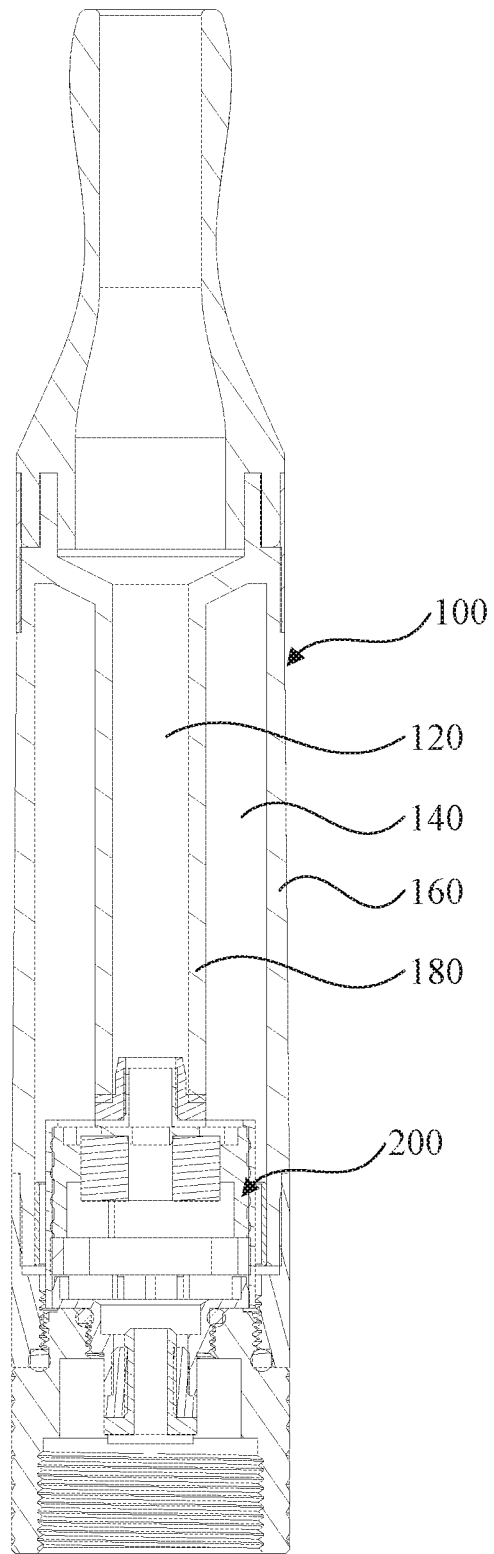
FIG. 3 is a cross-sectional view of the electronic cigarette of FIG. 2.

Referring to FIGS. 1 to 3, an electronic cigarette 1 according to an embodiment includes an atomizing assembly 10, and a power supply assembly 20 connected to the atomizing assembly 10. In one embodiment, the power supply assembly 20 is removably connected to the atomizing assembly 10. The atomizing assembly 10 includes a housing 100 and an atomizing core 200 connected to the housing 100. The housing 100 defines an airflow channel 120 and has a reservoir 140 surrounding the airflow channel 120 for storing liquid.

Figure 4:
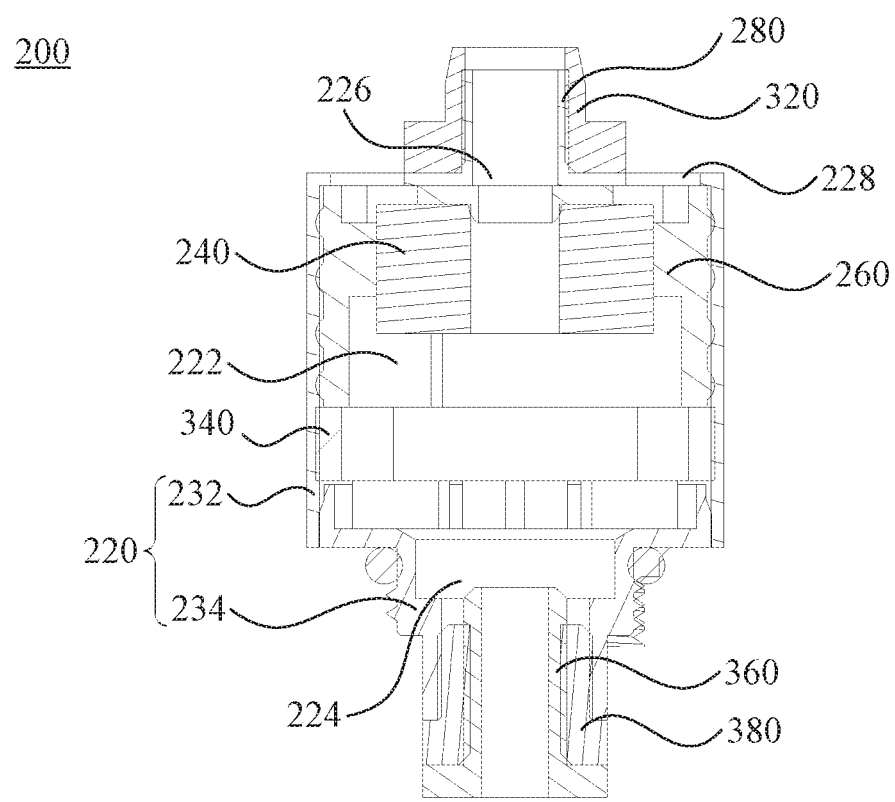
FIG. 4 is an enlarged cross-sectional view of an atomizing core shown in FIG. 3.
Figure 5:
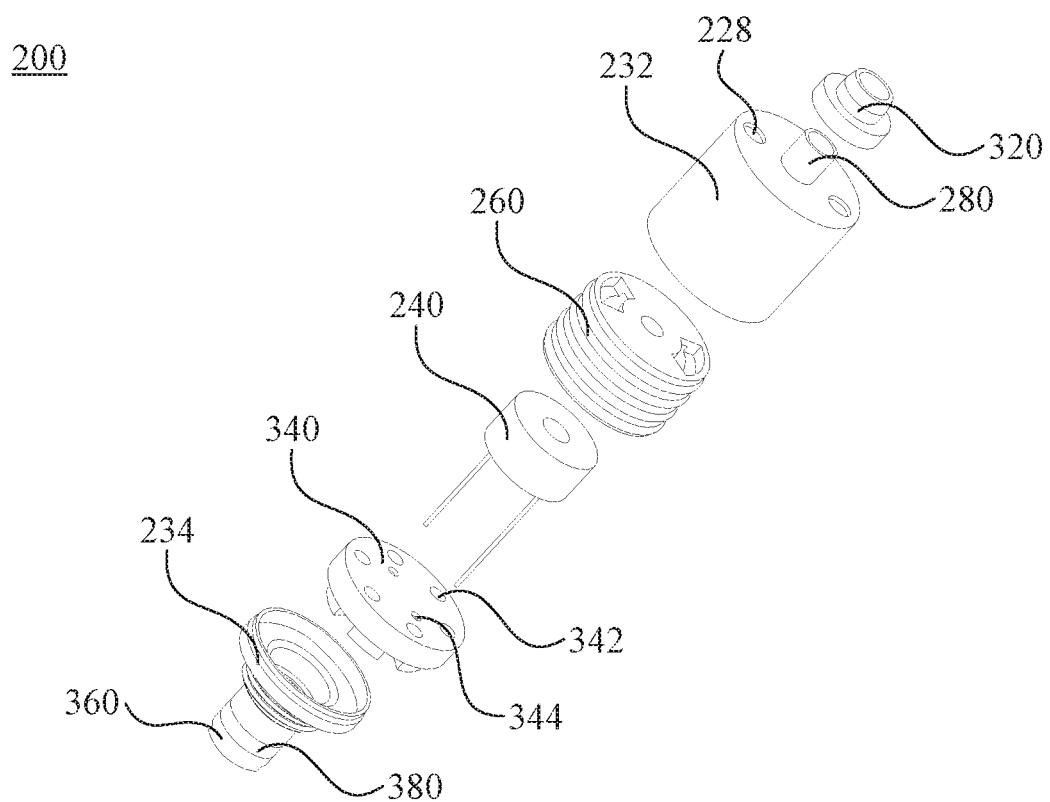
FIG. 5 is an exploded, perspective view of the atomizing core of FIG. 4.
Figure 6:
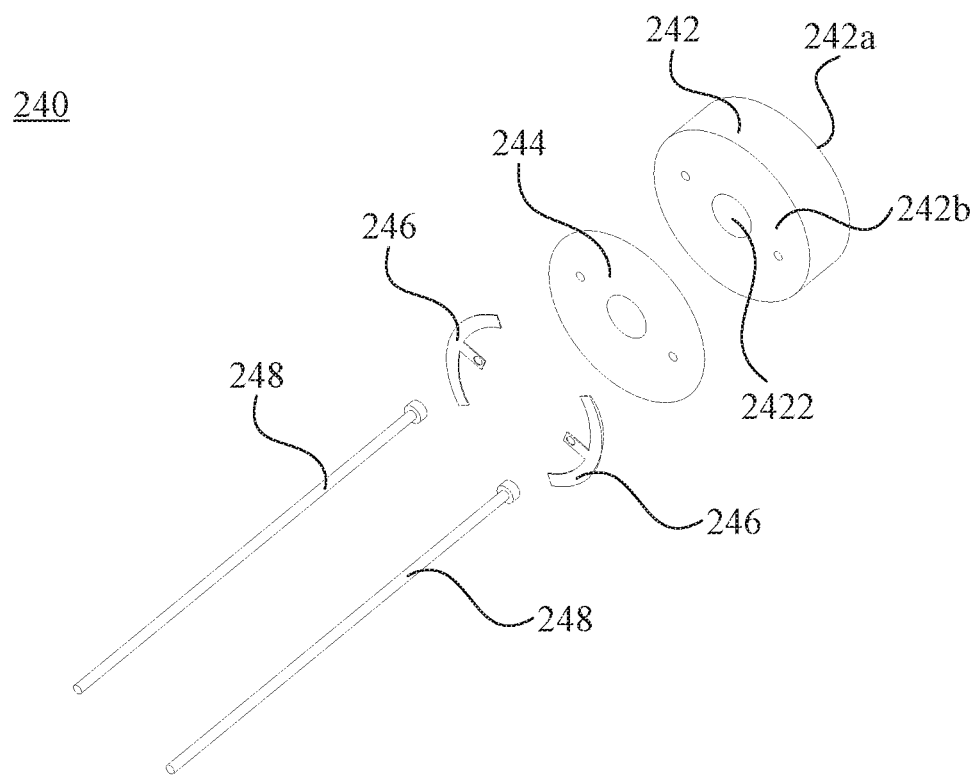
FIG. 6 is an exploded, perspective view of an atomizing element of FIG. 5.

Referring also to FIG. 4 and FIG. 5, the atomizing core 200 includes an atomizing element 240 configured to atomize the liquid. Referring to FIG. 6, the atomizing element 240 includes a porous body 242 and a porous heating film 244, both of which are provided with a plurality of micropores thereon. The porous body 242 includes a liquid absorbing surface 242a and an atomizing surface 242b. The porous heating film 244 is formed on the atomizing surface 242b. The airflow channel is in fluid communication with the atomizing surface 242b, and the reservoir 140 is in fluid communication with the liquid absorbing surface 242a.

Specifically, in one embodiment, the atomizing core 200 further includes a core body 220, which defines an atomizing chamber 222 therein. The core body 220 further defines an inlet 224 and an outlet 226 thereon, which are in fluid communication with the atomizing chamber 222. The outlet 226 is in fluid communication with the airflow channel 120. The atomizing element 240 is received inside the atomizing chamber 222. The core body 220 further defines a liquid absorbing hole 228 in fluid communication with the atomizing chamber 222 and the reservoir 140, and the liquid from the reservoir 140 can reach the liquid absorbing surface 242a of the porous body 242 through the liquid absorbing hole 228.

The working principle of the atomizing unit 10 of the present embodiment can be described as follows: firstly, the liquid enters the porous body 242 through the liquid absorbing hole 228, the porous heating film 244 then atomizes the liquid in the porous body 242 into smoke, the generated smoke flows along with the airflow and passes through the outlet 226 and the airflow channel 120, and is finally inhaled by the user.

In one embodiment, the plurality of micropores on the porous body 242 has a diameter of about 1 μm to about 100 μm. In another embodiment, a sum volume of the micropores on the porous body 242 having a diameter of about 5 μm to about 30 μm is more than 60% of a sum volume of total micropores on the porous body 242. The porous body 242 can perform a "blocking" effect for it can make sure the liquid cannot flow to the porous heating film 244 too quickly, meanwhile, it can guide the liquid to be infiltrated slowly onto the contact surface with the porous heating film 244. The diameter range of the micropores can enable the porous body 242 to have a better blocking effect which can prevent leakage of the liquid and a better guiding effect to prevent boil away of the liquid.

In one embodiment, the porous body 242 has a porosity of about 30% to about 83%. The porosity is a measure of the void (i.e., "empty") spaces in a material, and is a fraction of the volume of voids over the total volume. The porosity of the porous body 242 can be adjusted in accordance with the composition of the liquid for the electronic cigarette 1, for example, the porosity can be a little higher as long as the liquid has a larger viscosity, thus ensuring a better liquid guiding effect.

In addition, in one embodiment, the porous heating film 244 can be made of metal, such as one of titanium, nickel, or nickel-chromium. The porous heating film 244 has a thickness of about 0.5 μm to about 1.5 μm, preferably from about 0.8 μm to about 1 μm. The plurality of micropores formed on the porous heating film 244 has a diameter of about 5 μm to about 30 μm. The plurality of micropores on the porous heating film 244 can increase a contact area for the liquid, thus enhancing an atomizing effect. Since the porous heating film 244 is located on the surface of the porous body 242, the atomized liquid can easily flow out of the porous body 242. The porous heating film 244 can ensure a uniform heating to the surface of the porous body 242, such that the temperature of the porous body 242 evenly increases at all part, and the problem of generating large atomized particles due to low temperature at local portion can be avoided, thus the taste of the electronic cigarette 1 can be improved due to the uniform atomized particles.

The porous heating film 244 can be formed on the porous body 242 by vapor deposition, such that the porous heating film 244 can have a certain thickness while maintaining porous. The diameter of the plurality of micropores on the porous body 242 is greater than a thickness of the porous heating film 244, such that the porous heating film 244 will not block the micropores during vapor deposition of the porous heating film 244. Specifically, the vapor deposition can include chemical vapor deposition and physical vapor deposition method, such as evaporation, or sputtering.

In the illustrated embodiment, the porous body 242 can be made of porous ceramic. The porous ceramic is chemically stable and does not react chemically with the liquid. In addition, the porous ceramic is heat-resisting and can hardly be affected by the heat of the porous heating film 244. Furthermore, the porous ceramic is an insulator, which will not be electrically connected to the porous heating film 244, and it is easy to manufacture and has a lower cost. In an alternative embodiment, the porous body 242 can be made of other porous medium containing pores, such as porous glass, porous plastic, or porous metal. When the porous body 242 is made of porous plastic with a low temperature resistance, a heat insulating material layer can be formed on the porous body 242 before depositing the porous heating film 244. When the porous body 242 is made of conductive porous metal, an insulation material layer can be formed on the porous body 242 before depositing the porous heating film 244, for example, an oxidation treatment or the like can be performed on the surface of the porous heating film 244.

Referring to FIG. 4 and FIG. 5, in one embodiment, the atomizing core 200 further includes a first sealing element 260, which is received in the atomizing chamber 222. Therefore a gap between an inner sidewall of the core body 220 and the porous body 242 can be sealed by the first sealing element 260, and the porous heating film 244 is isolated from the liquid absorbing hole 228. In one embodiment, the core body 220 includes a supporting portion 232. The inlet 224 is located on the bottom side of the supporting portion 232. The porous body 242 defines a vent 2422 in fluid communication with the inlet 224. The first sealing element 260 seals the gap between the porous body 242 and the sidewall of the supporting portion 232.

In one embodiment, the core body 220 further includes a connecting portion 234 made of conducting material connected to the supporting portion 232. The inlet 224 is located on the connecting portion 234. The atomizing core 200 further includes an outlet pipe 280 and an insulating sleeve 320. The outlet pipe 280 is made of conducting material and is located at the inlet 224. The insulating sleeve 320 is positioned between the outlet pipe 280 and the second tubular structure 180, thus insulating the outlet pipe 280 from the second tubular structure 180. The connecting portion 234 is configured to be electrically coupled to a negative of the atomizing element 240 and the power supply assembly 20, the outlet pipe 280 is configured to be coupled to a positive of the atomizing element 240 and the power supply assembly 20. The insulating sleeve can be generally made of an elastic silicone material which has a sealing effect.

Referring to FIG. 6 again, in one embodiment, the atomizing element 240 further includes two electrodes 246 and two wires 248. The two electrodes 246 are electrically coupled to the porous heating film 244. In addition, in one embodiment, the two electrodes 246 are opposite configured and located adjacent to the edge of the porous heating film 244. The wires 248 are electrically coupled to the electrodes 246 by brazing technology, and at least partial wire 248 extends inside the porous body 242, thus ensuring a secured connection. One wire 248 coupled to one electrode 246 is located between the outlet pipe 280 and the insulating sleeve 320, while the other wire 248 coupled to another electrode 246 can be located between the insulating sleeve 320 and the connecting portion 234. The wires 248 are pressed by the elastic insulating sleeve 320, thus ensuring a secured connection.

Referring to FIG. 4, FIG. 5, in one embodiment, the atomizing core 200 further includes a liquid stopper 340, which is located between the atomizing element 240 and the inlet 224. When the liquid is absorbed by the porous body 242, the liquid may leak out from the atomizing element in case of vibration, then the liquid stopper 340 can prevent the liquid from flowing out through the inlet 224. During normal use of the electronic cigarette 1, the airflow can pass through the liquid stopper 340, and the liquid dropped on the liquid stopper 340 can be brought to the porous heating film 244 by the airflow for atomizing, thus further preventing leakage. The liquid stopper 340 defines a plurality of though holes 342 thereon having a diameter of about 1 mm to about 1.5 mm, which can prevent the liquid from flowing out effectively due to the surface tension. The liquid stopper 340 can be made of plastic, silicon and the like. In one embodiment, the liquid stopper 340 further defines a wiring hole 344 thereon allowing the wires 248 to pass through. The wiring hole 344 can be used to restrain the location of the wires 248, so as to avoid a short circuit.

Referring to FIG. 3, in one embodiment, the housing 100 includes a first tubular structure 160 and a second tubular structure 180. The first tubular structure 160 has a greater diameter than that of the second tubular structure 180, thus the second tubular structure 180 can be located inside the first tubular structure 160. The airflow channel 120 is formed inside the second tubular structure 180, and the reservoir 140 is formed between the first tubular structure 160 and the second tubular structure 180. Referring to FIG. 4 and FIG. 5, in one embodiment, the atomizing core 200 further includes an inlet pipe 360 and a second sealing element 380. The inlet pipe 360 is located at the inlet 224. The second sealing element 380 is sleeved on the inlet pipe 360, and partial inlet pipe 360 extends beyond the second sealing element 380.

In the illustrated embodiment shown in FIGS. 1 to 6, the opposite surfaces of the porous body 242 serve as the liquid absorbing surface 242a and the atomizing surface 242b, however, the configuration of the liquid absorbing surface 242a and the atomizing surface 242b may not be limited to this, for instance, the liquid absorbing surface 242a can be positioned on the sidewall of the porous body 242, and the atomizing surface 242b can be positioned on the inner sidewall of the vent 2422 of the porous body 242, as long as the atomizing surface 242b is in contact with the airflow passing through the electronic cigarette 1. The number of the liquid absorbing surface 242a and the atomizing surface 242b can both be plural.

Figure 7:
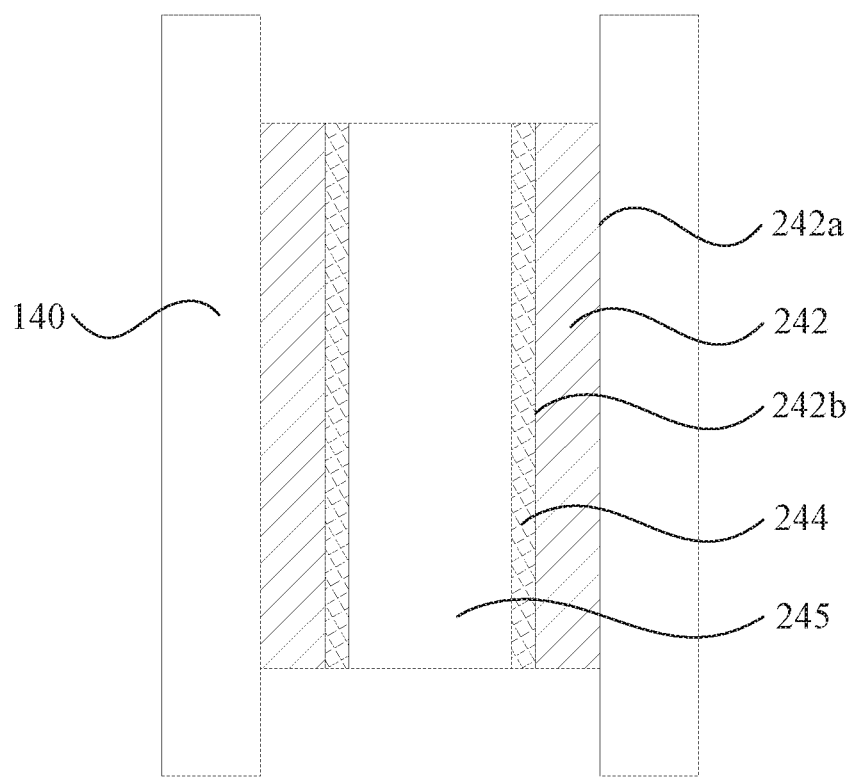
FIG. 7 is a cross-sectional view of an atomizing element in accordance with another embodiment.
Figure 8:
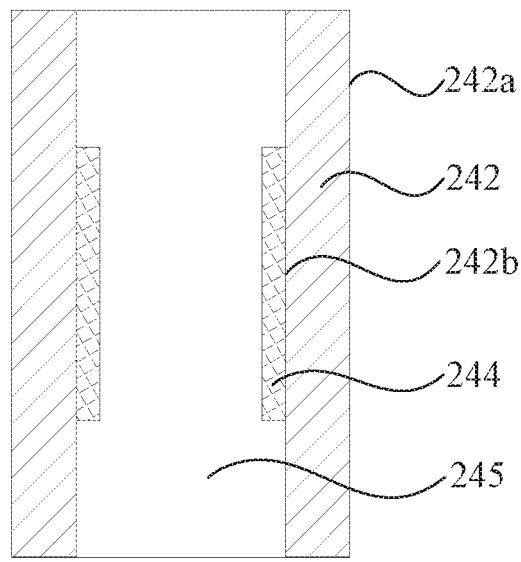
FIG. 8 is a cross-sectional view of an atomizing element in accordance with yet another embodiment.

Referring to FIG. 7, in one embodiment, the porous body 242 has a tubular shape, the liquid absorbing surface 242a is an outer surface of the porous body 242; the atomizing surface 242b is an inner surface of the porous body 242. The reservoir 140 can surround the porous body 242, the airflow channel 120 is in fluid communication with an cavity 245 of the porous body 242. In the illustrated embodiment shown in FIG. 7, the porous heating film 244 covers the whole atomizing surface 242b. In alternative embodiment, referring to FIG. 8, the porous heating film 244 may cover partial atomizing surface 242b.

Figure 9:
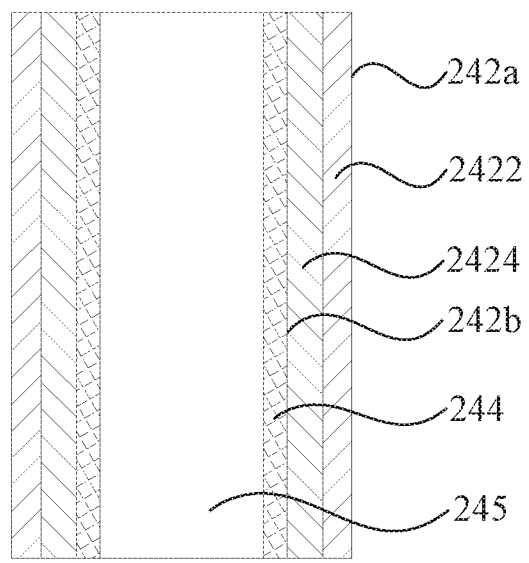
FIG. 9 is a cross-sectional view of an atomizing element in accordance with yet another embodiment.

Referring to FIG. 9, in one embodiment, the porous body 242 has a tubular shape and includes a first porous body 2422 and a second porous body 2424, which are connected together. The porous body 2422 is sleeved on the second porous body 2424. The liquid absorbing surface 242a is located on the first porous body 2422, and the atomizing surface 242b is located on the second porous body 2424. At least one of materials, diameter of micropores, and porosities of the first porous body 2422 and the second porous body 2424 are different. For example, in one embodiment, the first porous body 2422 can be made of metal, the second porous body 2424 can be a porous insulating layer formed by the oxidation treatment, such that the first porous body 2422 is insulated from the porous heating film 244. In an alternative embodiment, the diameters of the micropores on the first porous body 2422 is greater than the diameters of the micropores on the second porous body 2424, such that the first porous body 2422 has a better liquid storage capacity, while the second porous body 2424 has a better liquid guiding performance, further ensuring a better blocking effect and guiding effect of the porous body 242.

Figure 10:
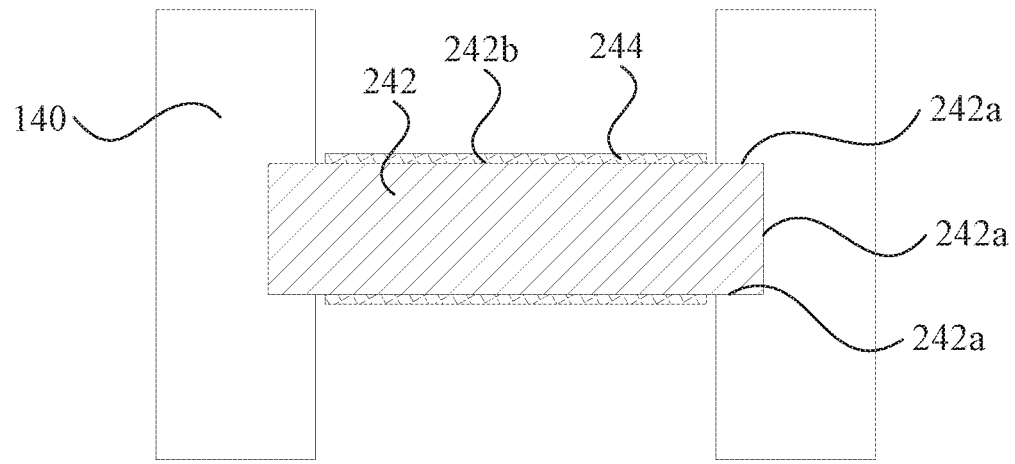
FIG. 10 is a cross-sectional view of an atomizing element in accordance with yet another embodiment.
Figure 11:
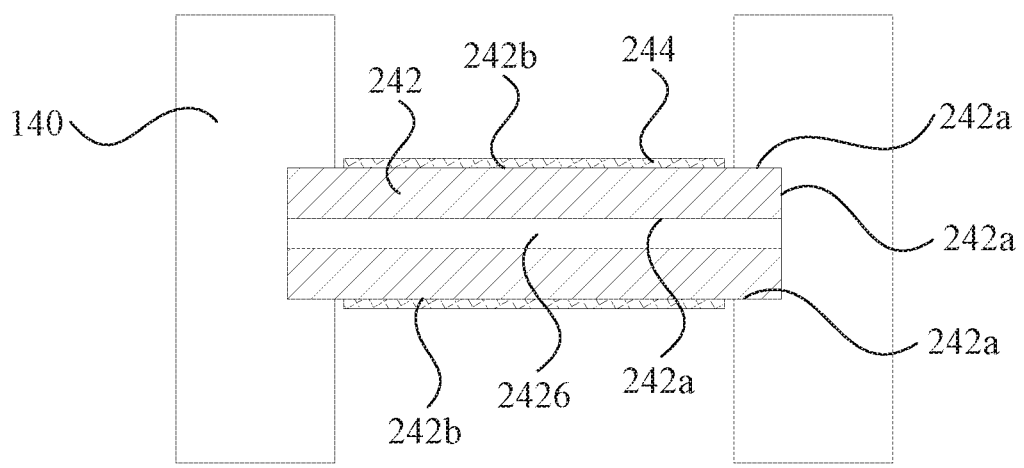
FIG. 11 is a cross-sectional view of an atomizing element in accordance with yet another embodiment.

Referring to FIG. 10, in one embodiment, the porous body 242 can have a columnar shape, such as cylindrical or prismatic. Both ends of the porous body 242 extends inside the reservoir 140, such that the middle portion of the porous body 242 is located inside the atomizing chamber 222. In this case, the liquid absorbing surface 242a is a part of sidewall of the porous body 242 close to both ends thereof; and the atomizing surface 242b is the rest of sidewall of the porous body in the middle thereof. Referring also to FIG. 11, in one embodiment, the porous body 242 defines a liquid communication hole 2426 extending axially. In this case, an inner surface of the liquid communication hole 2426 also functions as the liquid absorbing surface 242a, thus the area of the liquid absorbing surface 242a is increased, and the liquid guiding ability is improved.

Although the present invention has been described with reference to the embodiments thereof and the best modes for carrying out the present invention, it is apparent to those skilled in the art that a variety of modifications and changes may be made without departing from the scope of the present invention, which is intended to be defined by the appended claims.

What is claimed is:

1. An atomizing element for an electronic cigarette, comprising:
   a porous body comprising opposing first and second sides and a sidewall that extends therebetween, the porous body comprising a liquid absorbing surface on the first side and an atomizing surface on the second side; and
   a porous heating film formed on the atomizing surface by vapor deposition;
   wherein the porous body is provided with a plurality of micropores wherein the porous body is made of porous ceramic and insulated from the porous heating film;
   wherein a diameter of the plurality of micropores on the porous body is greater than a thickness of the porous heating film.

2. The atomizing element according to claim 1, wherein the porous body has a first opening that is contained within the body and that extends through the body, the porous heating film has a second opening that is aligned with the first opening in the porous body.

3. The atomizing element according to claim 1, wherein most of the plurality of the micropores has a diameter of about 1 μm to about 100 μm.

4. The atomizing element according to claim 3, wherein a sum volume of the micropores having a diameter of about 5 μm to about 30 μm is more than 60% of a sum volume of total micropores.

5. The atomizing element according to claim 1, wherein the porous body has a porosity of about 30% to about 83%.

6. The atomizing element according to claim 1, wherein the porous heating film is made of metal; the porous heating film has a thickness of about 0.5 μm to about 1.5 μm; the porous heating film is provided with a plurality of micropores having a diameter of about 5 μm to about 30 μm.

7. The atomizing element according to claim 6, wherein the porous heating film is made of one selected from the group consisting of titanium, nickel, and nickel-chromium; the thickness of the porous heating film ranges from about 0.8 μm to about 1 μm.

8. The atomizing element according to claim 1, further comprising:
   at least two electrodes electrically coupled to the porous heating film;
   a wire electrically coupled to the electrodes by brazing technology, wherein at least partial wire extends inside the porous body.

9. The atomizing element according to claim 1, wherein the porous body comprises a first porous body, and a second porous body connected to the first porous body, the liquid absorbing surface is located on the first porous body, the atomizing surface is located on the second porous body; wherein at least one of materials, diameter of micropores, and porosities of the first porous body and the second porous body are different.

10. The atomizing element according to claim 1, wherein the atomizing surface and the liquid absorbing surface are opposite surfaces of the porous body.

11. The atomizing element according to claim 1, wherein the porous body has a tubular shape; the liquid absorbing surface is an outer surface of the porous body; the atomizing surface is an inner surface of the porous body; the porous heating film covers at least partial atomizing surface.

12. The atomizing element according to claim 1, wherein the porous body has a columnar shape; the liquid absorbing surface is a part of sidewall of the porous body close to both ends thereof; the atomizing surface is the rest of sidewall of the porous body in the middle thereof.

13. The atomizing element according to claim 11, wherein the porous body defines a liquid communication hole extending axially; an inner surface of the liquid communication hole also functions as the liquid absorbing surface.

14. A method of manufacturing an atomizing element for an electronic cigarette, comprising:
   providing a porous body comprising opposing first and second sides and a sidewall that extends therebetween, the porous body comprising a liquid absorbing surface on the first side and an atomizing surface on the second side, wherein the porous body is provided with a plurality of micropores;
   forming a porous heating film on the atomizing surface by vapor deposition, wherein the diameter of the plurality of micropores on the porous body is greater than a thickness of the porous heating film, wherein the porous body is made of porous ceramic and insulated from the porous heating film.

15. The method according to claim to claim 14, wherein the porous body is made of porous plastic, and the method further comprises forming a heat insulating material layer on the porous body prior to forming the porous heating film.

16. The method according to claim to claim 14, wherein the porous body is made of conductive porous metal, and the method further comprises forming an insulation material layer on the porous body prior to forming the porous heating film.

17. The method according to claim to claim 14, wherein a sum volume of the micropores having a diameter of about 5 μm to about 30 μm is more than 60% of a sum volume of total micropores.

18. The method according to claim to claim 14, wherein the porous body has a porosity of about 30% to about 83%.

19. The method according to claim to claim 14, wherein the porous heating film is made of one selected from the group consisting of titanium, nickel, and nickel-chromium; the thickness of the porous heating film ranges from about 0.8 μm to about 1 μm.

20. An electronic cigarette, comprising:
   a power supply assembly;
   an atomizing assembly, comprising:
      a housing defining an airflow channel therein and comprising a reservoir for storing liquid; and
      an atomizing core connected to the housing, wherein the atomizing core comprises an atomizing element separated from the reservoir and with a porous body with opposing first and second sides and a sidewall that extends therebetween, the porous body is positioned in the housing with the first side facing towards the reservoir and the second side facing away from the reservoir, the porous body further comprises an atomizing surface on the second side and a liquid absorbing surface on the first side, the atomizing element also comprises a porous heating film formed on the atomizing surface by vapor deposition;
   wherein the airflow channel is in fluid communication with the atomizing surface, and the reservoir is in fluid communication with the liquid absorbing surface;
   wherein the porous body is provided with a plurality of micropores, wherein the porous body is made of porous ceramic and insulated from the porous heating film;
   wherein the diameter of the plurality of micropores on the porous body is greater than a thickness of the porous heating film;

wherein the power supply assembly is electrically coupled to the atomizing element of the atomizing assembly.

* * * * *